United States Patent [19]

Crouther et al.

[11] Patent Number: 5,441,759
[45] Date of Patent: Aug. 15, 1995

[54] METHOD TO STABILIZE TDMAC HEPARIN COATING

[75] Inventors: Ron Crouther, Chesterfield; Daniel P. Flynn, Florissant; Elizabeth Lagwinska, Chesterfield, all of Mo.

[73] Assignee: Sherwood Medical Company, St. Louis, Mo.

[21] Appl. No.: 255,288

[22] Filed: Jun. 8, 1994

Related U.S. Application Data

[63] Continuation of Ser. No. 940,421, Sep. 3, 1992, abandoned.

[51] Int. Cl.⁶ .................. B05D 3/06; B05D 1/18; B05D 3/02
[52] U.S. Cl. .................. 427/2.3; 427/2.28; 427/2.25; 427/551
[58] Field of Search ............ 427/496, 501, 551, 595, 427/2.3, 2.12, 2.28, 2.25, 379

[56] References Cited

U.S. PATENT DOCUMENTS

| | | | |
|---|---|---|---|
| 3,453,194 | 7/1969 | Bennett et al. | 427/2 |
| 3,617,344 | 11/1971 | Leininger et al. | 427/430.1 |
| 3,713,860 | 1/1973 | Auskern | 427/2 |
| 3,844,989 | 10/1974 | Harumiya et al. | 260/17.4 R |
| 3,955,012 | 5/1976 | Okamura et al. | 427/580 |
| 3,976,081 | 8/1976 | Lapidot | 128/350 R |
| 4,055,682 | 10/1977 | Merrill | 427/496 |
| 4,308,232 | 12/1981 | Crouther et al. | 422/102 |
| 4,326,532 | 4/1982 | Hammar | 128/349 R |
| 4,331,697 | 5/1982 | Kudo et al. | 427/2 |
| 4,713,402 | 12/1987 | Solomon | 523/112 |

FOREIGN PATENT DOCUMENTS

| | | | |
|---|---|---|---|
| 46-37433 | 11/1971 | Japan | 427/496 |
| 56-108707 | 8/1981 | Japan | 427/2 |
| 1-299564 | 12/1989 | Japan | 427/2 |

OTHER PUBLICATIONS

Chawla and Chang, Biomaterials, Medical Devices and Artificial Organs, "Nonthrombogenic Surface of Heparin", dated 1974, pp. 157–169, (no month available).

Chawla and Hayward, Pharmacology, "Effect of Gamma Radiation on Heparin", dated 1980, pp. 224–228, (no month available).

*Primary Examiner*—Diana Dudash
*Attorney, Agent, or Firm*—Montgomery W. Smith; Curtis D. Kinghorn; Ari M. Bai

[57] ABSTRACT

A medical device is coated with a solution of TDMAC heparin and then allowed to air dry. Thereafter, the coated medical device is exposed to gamma ray radiation. The gamma radiation strengthens the bond of the TDMAC to the material of the medical device. In a variation of this method, TDMAC heparin coated and gamma ray irradiated medical device is heated for an extended period of time. This heating has been found to further strengthen the bond of the TDMAC heparin to the medical device.

19 Claims, No Drawings

METHOD TO STABILIZE TDMAC HEPARIN COATING

This is a continuation of application Ser. No. 07/940,421, filed on Sep. 3, 1992, now abandoned.

BACKGROUND OF THE INVENTION

1. Field of the Invention

The instant invention relates to a method for stabilizing a heparin coating to a medical device and more particularly to a method for stabilizing a TDMAC heparin coating to a medical device made of polyvinylchloride (PVC).

2. Description of Related Art

Heparin is a anticoagulant substance which is often applied to the surface of medical devices used in the blood stream to prevent the formation of blood clots. Many medical devices are made of polyvinylchloride (PVC). Heparin may be bound directly to the surface of the PVC device. However, it has been found that heparin has better anti-thrombogenic properties when the heparin molecule is spaced away from the PVC surface. Molecules such as tridodecylmethyl ammonium chloride (TDMAC) and PEO-polyethylene oxide, among others, are used to space the heparin molecule away from the PVC surface and also to bind the heparin molecule to the PVC.

The standard practice for applying TDMAC heparin to a medical device is to first fabricate a medical device made of PVC. The medical device is then dipped in a one to one mixture of toluene/petroleum ether containing a TDMAC heparin complex in, for example, the amount of 1.25-2% by weight for typically about 30 seconds. The coated medical device is then allowed to air dry at room temperature.

The process of binding heparin to TDMAC is believed to be a weak ionic bond. Moreover, the TDMAC material is believed to bind on contact to the PVC material through weak van der Waals bonds. Consequently, it is relatively easy to break the van der Waals bonds thereby removing the TDMAC and its weakly ionic bonded heparin from the medical device.

The PEO-polyethylene oxide molecule bonds to both the heparin and PVC with relatively stronger covalent bonds. As a result, heparin is more strongly bound to PVC with PEO-polyethylene oxide than it is with TDMAC. However, the process of binding the heparin to PVC with PEO-polyethylene oxide is much more complicated than the one step dip process described above to bind heparin to PVC with TDMAC.

Although heparin may be spaced away from and bound to a PVC medical device with TDMAC, when used in the body, the heparin can still be dissolved from the medical device over time. Particularly where the medical device will remain in the patient's body for an extended time, it is desirable to retain the heparin on the medical device for as long as possible in order to minimize the formation of blood clots. In addition, it is preferred that the material binding the heparin to the medical device, in this case TDMAC, not be released into the patient.

Medical devices are also made of polyurethane or silicone. Like PVC, heparin may also be either directly bound or bound through spacer molecules to polyurethane or silicone polymer material. Again, as with medical devices made of PVC, it has been found that heparin has better antithrombogenic properties when the heparin molecule is spaced away from the surface of the polyurethane or silicone.

A disadvantage of using polyurethane or silicone to make medical devices is that polyurethane and silicone are more expensive and difficult to process than PVC. In addition, PVC has additional advantages over polyurethane or silicone. Unlike polyurethane or silicone, PVC is extremely thermosensitive. In particular, PVC can be relatively rigid at room temperature for placement in the patient and then soften dramatically as the medical device warms to body temperatures for increased comfort and reduced trauma to the patient. Further, by varying the percentage of resin to plasticizers, PVC can be made in a variety of stiffnesses to provide a desired balance of physical properties.

An additional benefit to using PVC is that it can be readily compounded with high levels of radiopaque agents making the resulting medical device easily discernible under X-ray or fluoroscopy. In addition, unlike silicone, catheter tips made of PVC can be melt formed to a smooth round shape and tapered tubes., including those with integral connectors, can be easily formed.

In view of the foregoing, it is desirable to strongly bond heparin to PVC through a spacer molecule that is easily applied to the PVC so that medical devices used in the blood stream, particularly devices that will remain in the blood stream for an extended period, may be made of PVC.

SUMMARY OF THE INVENTION

A medical device made of PVC is coated with a solution of TDMAC heparin and then allowed to air dry. Thereafter, the coated medical device is exposed to gamma radiation. The gamma radiation strengthens the bond of the TDMAC heparin to the material of the medical device.

In a variation of this method, the gamma ray irradiated medical device and TDMAC heparin coating is heated for an extended period of time. This heating has been found to further strengthen the bond of the TDMAC heparin to the medical device.

An additional benefit of irradiating the medical device and TDMAC heparin coating with gamma radiation is that the medical device is sterilized without the use of ethylene oxide (ETO) gas, with its concomitant problems.

It is therefore an object of the instant invention to provide a method for strongly bonding the TDMAC heparin to the medical device.

It is another object of the instant invention to provide a method for bonding TDMAC heparin to a medical device which also sterilizes the medical device.

It is another object of the instant invention to attach heparin to PVC through a spacer molecule through a process that is simple and easy to implement.

It is a further object of the instant invention to provide a method for bonding TDMAC heparin to a medical device which is relatively inexpensive.

It is a further object of the instant invention to provide a method for bonding TDMAC heparin to a medical device which does not significantly affect the structural integrity of the medical device.

These and other objects of the instant invention will be clear from the description contained herein and more particularly with reference to the following detailed description.

DETAILED DESCRIPTION OF THE INVENTION

The instant invention comprises a method for strongly attaching TDMAC heparin to a surface of a medical device. The medical device is preferably made of a polyvinylchloride (PVC) material. However, it is believed the method described herein may also be applied to a medical device made of polyurethane or silicone.

In order to apply the method of the instant invention, a medical device must first be fabricated. Representative medical devices include, but are not limited to, catheters, shunts, cannulae, tubing and other devices used in contact with blood. The medical device is then dipped in a one to one mixture of toluene/petroleum ether containing a 1.25–2% by weight solution of TDMAC heparin for approximately 30 seconds. This allows the TDMAC heparin solution to coat the surface of the medical device.

After dipping the medical device in the TDMAC heparin solution, the medical device is removed and allowed to air dry at room temperature.

The next step is to expose the TDMAC heparin coated and air dried medical device to gamma ray radiation. The amount of gamma ray radiation is that commonly used to sterilize medical devices. The common range of gamma radiation used to sterilize medical devices is about 0.5 to 3.5 megarads. However, the preferred range of exposure is from about 1.5 to about 2.5 megarads. Although the preferred range of gamma ray exposure is from about 1.5 to about 2.5 megarads, exposures as low as about 0.5 megarads and up to and including about 3.5 megarads are also believed to be effective. A common source of gamma ray radiation is Cobalt 60 although other sources of gamma ray radiation may be used as desired.

A consequence of irradiating the medical device with this particular amount of radiation is that the medical device is sterilized as a result of the exposure. Sterilization occurs in place of ethylene oxide (ETO) gas sterilization. By avoiding the use of ethylene oxide, there is no danger of residual toxic ethylene oxide or its by-products remaining in the packaging. Further, the common practice of aerating the packaging containing the ETO sterilized device for up to several weeks in order to remove the residual ETO gas or its by-products is eliminated. With the use of gamma ray radiation according to the instant invention, no aeration is required.

Further, the ETO gas is sometimes mixed with fluorocarbons such as freon to transport the ETO gas for sterilization to reduce the chance of explosion inherent with the highly flammable ETO gas. With present systems, the release of the freon gas is a problem. By eliminating the ETO, the release of freon, which is a suspected source of ozone depletion, is eliminated in these situations.

In saline or whole blood tests to determine the amount of TDMAC heparin retained on the medical device, when TDMAC heparin coated devices exposed to the gamma ray radiation according to the teachings of the instant invention are compared to TDMAC heparin coated devices not exposed to the gamma ray radiation, a significantly larger amount of TDMAC heparin coating is retained on the gamma ray irradiated medical device.

As stated above, it is believed that during the step of dipping the medical device in TDMAC heparin, the TDMAC bonds to the surface of the medical device by weak van der Waals bonds and the heparin to the TDMAC by ionic bonds. It is believed that the gamma ray radiation causes some crosslinking or covalent bonding between the heparin molecule and the TDMAC and surface molecules of the medical device, thereby increasing the strength of the bond between the TDMAC heparin and the medical device.

Further, studies have shown that after the exposure to the gamma ray radiation, the heparin molecule appears to retain its anticoagulant qualities.

An additional step after exposing the medical device to gamma ray radiation produces an even stronger bond for the TDMAC heparin molecule to the medical device. In this step, after removing the medical device from exposure to the gamma radiation, the coated and irradiated medical device is heated for an extended period of time. The preferred temperature is about 150° F. and the preferred time is about three days. The preferred heating method is forced air heating although other methods of heating may be used.

When the medical device is made of PVC, because PVC material is sensitive to heat, during exposure to the higher temperature the physical properties of the PVC changes in such a way that the TDMAC heparin molecule bonds more strongly to the PVC. When the PVC cools, the bond between the PVC and the TDMAC heparin molecule formed at the elevated temperature remains strong. It has been found that by combining the gamma ray radiation according to the teachings of this disclosure with this heating, the TDMAC heparin molecule is even more securely bound to the medical device than by gamma irradiation alone. It is believed that a similar process is responsible for the stronger bonding of the TDMAC heparin molecule to the surface of medical devices made of polyurethane and silicone when the gamma ray irradiated medical device is thereafter heated according to the teachings of the invention.

In saline tests done to determine the strengths of the bonds binding the TDMAC heparin to the medical device in the method of irradiation and heating compared to just dipping the device in the TDMAC solution and allowing it to air dry, it has been found that four to five times less heparin is removed over comparable time periods.

PVC material of any composition is believed amenable to the method of the instant invention described herein. In particularly, PVC material having 100 parts resin and approximately 60 parts plasticizers as well as PVC having 100 parts resin and approximately 47 parts plasticizers were tested according to the disclosure contained herein. No significant difference was found in the bonding strength of the TDMAC heparin to the PVC material.

As described above, one step in the method disclosed herein is to coat the medical device with a coating of TDMAC heparin. The preferred way of coating the medical device is by dipping or immersing the medical device into a solution of TDMAC heparin. However, other means of coating the medical device with TDMAC heparin, such as will occur to those skilled in the art, are within the scope of the invention. Examples of such means include, but are not limited to, spraying, wiping, and painting of the TDMAC heparin onto the medical device.

Further, although the preferred way of creating a TDMAC heparin solution is to mix TDMAC heparin with toluene/petroleum ether, other solvents may be used instead of toluene/petroleum ether. In particular, other organic solvents and more particularly hydrocarbon solvents can be used in place of the toluene/petroleum ether.

Further, although the step of drying the TDMAC heparin coated device is preferably done by air drying the device at room temperature, other means of drying the medical device are within the scope of the invention. For example, the TDMAC heparin coated medical device may be dried by forced air heating or by oven drying to name but a few of the methods that will occur to those skilled in the art. It is clear that the temperature for drying the medical device may be elevated above normal room temperature.

The invention has been described in connection with a specific method. It is to be understood that the description contained herein is for the purpose of illustration and not for the purpose of limitation. Changes and modifications may be made to the description contained herein and still be within the scope of the invention. Further, obvious changes and modifications will occur to those skilled in the art.

We claim:

1. A method to stabilize a tridodecylmethyl ammonium chloride (TDMAC) heparin coating on a medical device comprising the steps of:
   coating the medical device with a TDMAC heparin solution;
   drying the TDMAC heparin solution on the coated medical device;
   irradiating the coated medical device with gamma ray radiation; and,
   heating the previously gamma ray irradiated medical device.

2. The method of claim 1 wherein the medical device is exposed to gamma radiation at an intensity of about 0.5 to about 3.5 megarads.

3. The method of claim 2 wherein the medical device is exposed to gamma radiation at an intensity of about 1.5 to about 2.5 megarads.

4. The method of claim 2 wherein the step of heating is performed at a temperature of about 150 F.

5. The method of claim 4 wherein the step of heating the previously gamma ray irradiated medical device comprises heating the medical device for about three days at a temperature of about 150° F.

6. The method of claim 5 wherein the step of heating the previously gamma ray irradiated medical device comprises heating the medical device for about three days at a temperature of about 150° F.

7. The method of claim 1 wherein the step of heating the previously gamma ray irradiated medical device includes heating the medical device for about three days.

8. The method of claim 1 wherein the step of heating the previously gamma ray irradiated medical device includes heating the medical device at a temperature of about 150° Fahrenheit.

9. The method of claim 1 wherein the step of heating the previously gamma ray irradiated medical device comprises heating the medical device for about three days at a temperature of about 150° Fahrenheit.

10. The method of claim 1 wherein the solvent of said TDMAC heparin solution is a mixture of toluene and petroleum ether.

11. The method of claim 10 wherein said solution comprises toluene/petroleum ether solvent in a one to one mixture by weight with TDMAC heparin in the amount of about 1.25–2% by weight of TDMAC heparin.

12. The method of claim 11 wherein said step of coating is performed for thirty seconds and includes coating the medical device in a solution comprising a one to one mixture of toluene/petroleum ether containing TDMAC heparin solution in the amount of about 1.25–2% by weight of TDMAC heparin.

13. The method of claim 1 wherein the step of coating the medical device includes immersing the medical device in said TDMAC heparin solution.

14. The method of claim 1 wherein the step of drying the coated medical device includes air drying the medical device.

15. The method of claim 1 wherein the step of drying the coated medical device includes drying the medical device at about room temperature.

16. The method of claim 1 wherein the step of drying the coated medical device includes air drying the medical device at about room temperature.

17. A method to stabilize a tridodecylmethyl ammonium chloride (TDMAC) heparin coating on a medical device comprising the steps of:
   coating the medical device with a TDMAC heparin solution comprising TDMAC heparin mixed with a solvent;
   air drying the coated medical device at about room temperature;
   irradiating the coated medical device with gamma ray radiation; and,
   heating the previously gamma ray irradiated medical device.

18. A method to stabilize a tridodecylmethyl ammonium chloride (TDMAC) heparin coating on a medical device comprising the steps of:
   immersing the medical device in a TDMAC heparin solution comprising a one to one mixture of weight of toluene/petroleum ether containing TDMAC heparin solution in the amount of about 1.25–2% by weight for about thirty seconds;
   air drying the coated medical device at about room temperature;
   exposing the coated medical device to gamma radiation at an intensity of about 0.5 to about 3.5 megarads; and,
   heating the previously gamma ray irradiated medical device for about three days at a temperature of about 150° Fahrenheit.

19. A method to stabilize a tridodecylmethyl ammonium chloride (TDMAC) heparin coating on a medical device made of polyvinylchloride (PVC) comprising the steps of:
   coating the medical device with a TDMAC heparin solution;
   drying the TDMAC heparin solution on the coated medical device;
   irradiating the coated medical device with gamma ray radiation; and,
   heating the previously gamma ray irradiated medical device.

* * * * *